US007172874B2

(12) United States Patent
Hollyfield et al.

(10) Patent No.: US 7,172,874 B2
(45) Date of Patent: Feb. 6, 2007

(54) DIAGNOSTIC METHODS FOR AGE RELATED MACULAR DEGENERATION

(75) Inventors: Joe G. Hollyfield, Beachwood, OH (US); Robert G. Salomon, Cleveland, OH (US); John W. Crabb, Chagrin Falls, OH (US); Xiaorong Gu, Lyndhurst, OH (US)

(73) Assignees: The Cleveland Clinic Foundation, Cleveland, OH (US); Case Western Reserve University, Cleveland, OH (US)

( * ) Notice: Subject to any disclaimer, the term of this patent is extended or adjusted under 35 U.S.C. 154(b) by 582 days.

(21) Appl. No.: 10/135,196

(22) Filed: Apr. 30, 2002

(65) Prior Publication Data

US 2004/0265924 A1 Dec. 30, 2004

Related U.S. Application Data

(60) Provisional application No. 60/287,543, filed on Apr. 30, 2001.

(51) Int. Cl.
*G01N 33/53* (2006.01)

(52) U.S. Cl. ....................... 435/7.1; 435/7.2; 435/7.92; 436/512; 436/513; 436/514; 436/536

(58) Field of Classification Search ................. 435/7.1, 435/7.2, 7.92; 436/512, 513, 514, 536
See application file for complete search history.

(56) References Cited

U.S. PATENT DOCUMENTS 5,686,250 A 11/1997 Salomon

OTHER PUBLICATIONS

Lecomte et al. J. Neurochemistry 1996 vol. 66, p. 2160.*
Bernoud-Hubac et al. J. Biological Chem 2001 vol. 276, p. 30964.*
Abstract 2109-B3555, "Oxidative Protein Modificatin in AMD from Docosahexaenoic Acid" by Crabb, et al., *Investigative Ophthalmology and Visual Science*, vol. 41, No. 4, Mar. 15, 2000.

* cited by examiner

*Primary Examiner*—Long V. Le
*Assistant Examiner*—Jacob Cheu
(74) *Attorney, Agent, or Firm*—Calfee, Halter & Griswold LLP

(57) ABSTRACT

Diagnostic methods for identifying a test subject who has or is at risk of developing age-related macular degeneration (AMD) or an analogous disease associated with oxidation of DHA-containing lipids are provided. In one aspect, the methods comprise: assaying for the presence of elevated levels of 2-(ω-carboxyethyl) pyrrole (CEP) adducts in a bodily fluid which has been obtained from the test subject. In a preferred embodiment, such methods comprise providing an antibody that is immunospecific for CEP, contacting a bodily fluid from the subject with the anti-CEP antibody, and assaying for the formation of a complex between the antibody and an antigen in the sample. In another aspect, the methods comprise assaying for the presence of elevated levels of an antibody that binds to or is immunospecific for a CEP adduct in the bodily fluid of the test subject. The present invention also relates to CEP protein and peptide adducts, an antibody reactive with a CEP adduct and a diagnostic kit comprising such antibody.

14 Claims, 7 Drawing Sheets

Protein-Bound CEP
protein
carboxyl
COOH
Protein-Bound CPP
protein
carboxyl
COOH

DIAGNOSTIC METHODS FOR AGE RELATED MACULAR DEGENERATION

This application which claims priority from U.S. Provisional Application Ser. No. 60/287,543, filed on Apr. 30, 2001.

This work was supported, at least in part, by grants GM21249 and HL53315 from the National Institutes of Health. The government has certain rights in this invention.

BACKGROUND OF THE INVENTION

This invention relates to novel methods for diagnosing and screening for age-related macular degeneration and analogous diseases associated with docosahexaenoic acid (DHA) containing lipids. More specifically, this invention relates to diagnostic methods for determining if an individual has or is at risk of developing age-related macular degeneration and atherosclerosis.

Macular degeneration is the clinical term used to describe those diseases that are characterized by a breakdown of the macula, the small portion of the retina responsible for central vision. Juvenile macular degeneration, also referred to as early onset macular degeneration occurs early in life, such as for example in the second and third decade, while age-related macular degeneration (AMD) occurs later in life, typically in the fifth decade and later. AMD constitutes a major health problem for individuals over 55 years of age in the industrialized world. In the USA alone between 6 and 10 million senior adults are legally blind from AMD.

It is desirable to have diagnostic methods for determining if an individual has a predisposition for developing age-related macular degeneration and other diseases which involve oxidative damage to tissues from oxidation of DHA-containing lipids.

SUMMARY OF THE INVENTION

In accordance with the present invention, diagnostic methods for identifying a test subject who has or is at risk of developing age-related macular degeneration (AMD) or an analogous disease associated with oxidation of DHA-containing lipids are provided. In one aspect, the methods comprise: assaying for the presence of elevated levels of 2-(ω-carboxyethyl) pyrrole (CEP) adducts in a bodily fluid which has been obtained from the test subject. As used herein the term "CEP adduct" refers to a molecule which comprises CEP bound to a carrier comprising a primary amino group. Examples of such carriers are a protein, an amino phospholipid, an amino sugar, an amino acid, particularly lysine, or a metabolic product of these molecules. As used herein, the term "test subject" refers to a mammal, preferably a human. In a preferred embodiment, such methods comprise providing an antibody that is immunospecific for CEP, contacting a bodily fluid from the subject with the anti-CEP antibody, and assaying for the formation of a complex between the antibody and an antigen in the sample. In another aspect, the methods comprise assaying for the presence of elevated levels of an antibody that binds to or is immunospecific for a CEP adduct in the bodily fluid of the test subject. Preferably, the level of one or both of the CEP-related diagnostic markers, i.e., the CEP adduct and the anti-CEP antibody, is determined in a bodily fluid obtained from the test subject and compared to the level of the diagnostic marker in a corresponding bodily fluid from normal healthy subjects.

In another aspect, the present invention comprises methods for monitoring progression of AMD or atherosclerosis in a test subject who is known to have AMD or atherosclerosis. Such methods comprise determining the levels of CEP adducts, anti-CEP antibodies, or both in bodily fluids taken from the test subject over successive time intervals. The levels of the CEP adducts or anti-CEP antibodies in the samples are compared to determine the prognosis of the disease in the subject. An increase in the levels of the diagnostic marker in a bodily fluid obtained from the test subject over time is indicative of increased oxidative damage to tissues from oxidation of DHA and a poor prognosis.

In another aspect, the present methods are used to monitor the response of the test subject to treatment with a therapeutic composition targeted at AMD, atherosclerosis, or another disease associated with oxidative damage to tissues from oxidation of DHA. Such methods comprise determining the levels of a CEP adduct, or anti-CEP antibody, or both in a bodily fluid obtained from the test subject before and after such treatment. Preferably, the concentration or content of one or both of these diagnostic markers is measured in samples taken over successive time intervals following treatment. A decrease in the levels of one or both of these markers following administration of an anti-AMD drug to the subject is indicative of decreased potential for oxidative damage to ocular tissues of the subject.

The present invention also relates to an antibody reactive with a CEP adduct and a diagnostic kit comprising such antibody. The present invention also relates to CEP protein and peptide adducts which are useful for assessing the levels of anti-CEP antibodies in a bodily fluid obtained from a test subject. The present invention also relates to methods of producing antibodies immuno-specific for CEP adducts and to methods of producing CEP protein and peptide adducts.

C. before hydrolysis; (B) products from reaction of HOHA-PC with HSA for 1 h (▲), 8 h (■), 24 h (♦) at 37° C. after hydrolysis.

Figure 7:
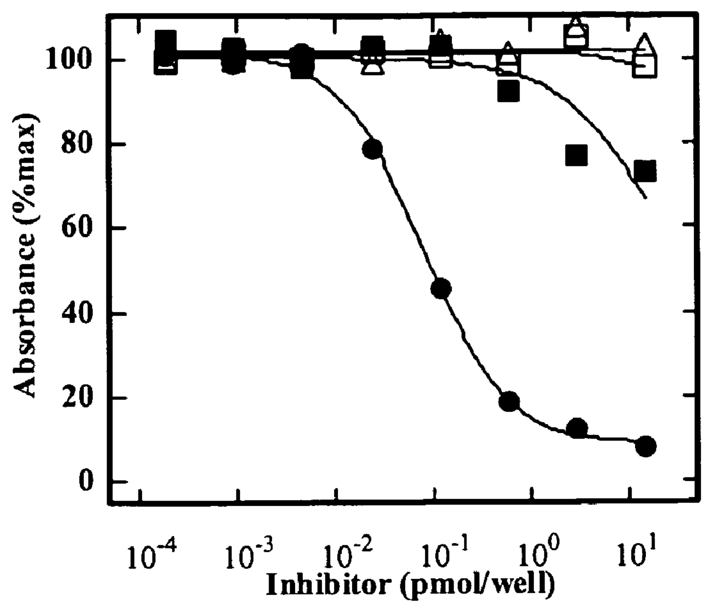

FIG. 7. Inhibition curve for binding of anti-CEP-KLH to CEP-BSA by CEP-HSA (●) and products from oxidation of DHA-PC in the presence of HSA for 1 h (▲), 8 h (♦), 24 h (□) at 37° C. after hydrolysis.

Figure 8:
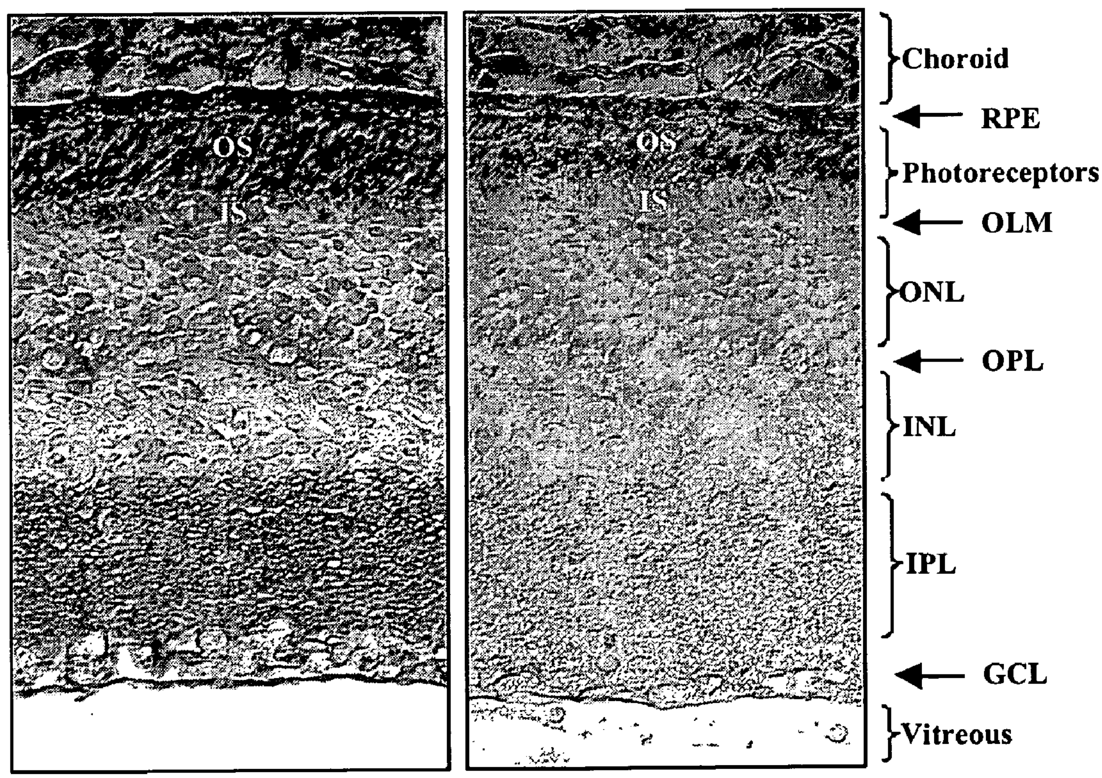

FIG. 8. CEP immunoreactivity in the mouse retina. Immunohistochemical staining of retina is prominent in the photoreceptor/retinal pigment epithelium (RPE) complex. In the photoreceptor layer, the outer segments (OS) are intensely stained while the photoreceptor inner segments (IS) are unlabeled. Less intense staining is also evident in the inner plexiform layer (IPL). Little staining is seen in the OLM (outer limiting membrane), ONL (outer nuclear layer), ONL (outer nuclear layer), OPL (outer plexiform layer), INL (inner nuclear layer), or GCL (ganglion cell layer).

Figure 9:
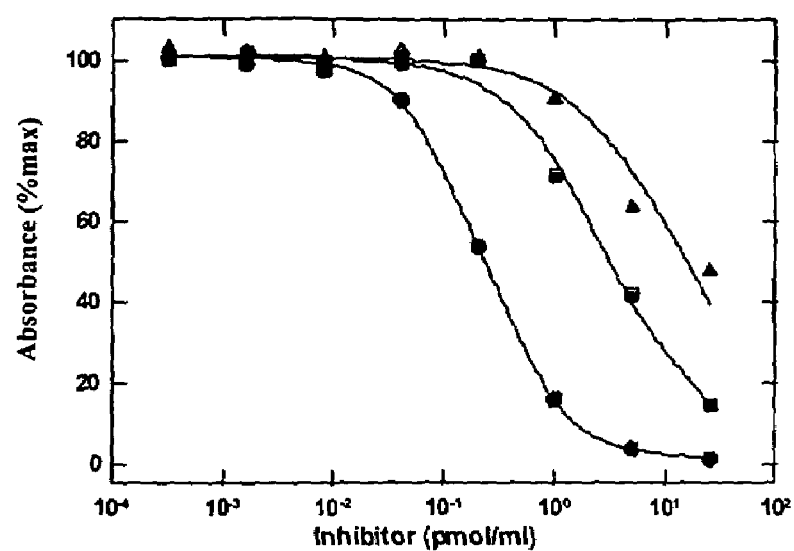

FIG. 9. Inhibition curves for binding of anti-CEP-KLH to CEP-BSA by CEP-HSA (●), plasma from an AMD patient (□), and a normal control (▲).

Figure 10:
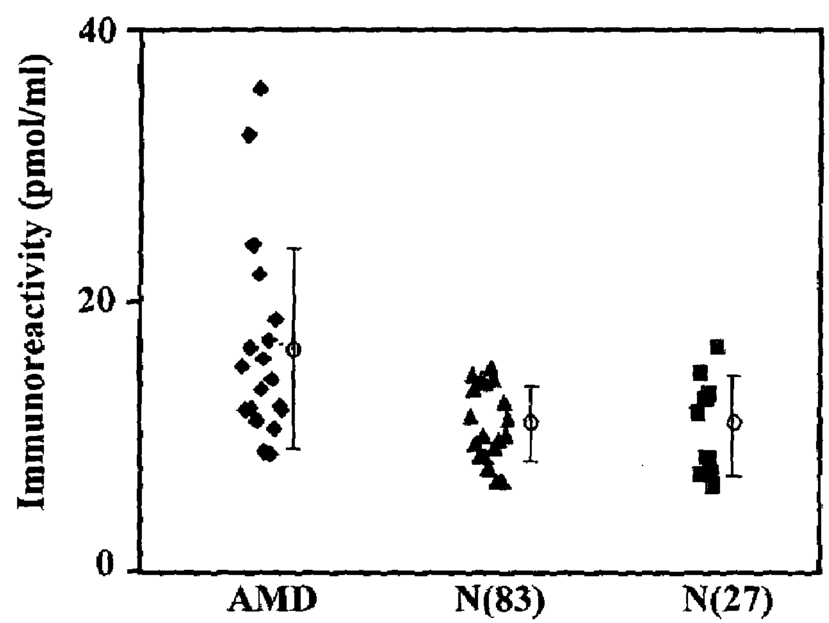

FIG. 10. Levels of CEP adduct immunoreactivity detected in human plasma from older volunteers who do not have AMD, (▲) N(83), younger healthy volunteers, (□) N(27), and patients who were diagnosed to have age-related macular degeneration, (♦) AMD. The figure also shows mean levels detected (O). The error bars indicate the standard deviation (S.D.) for each data set.

Figures 11, 12:
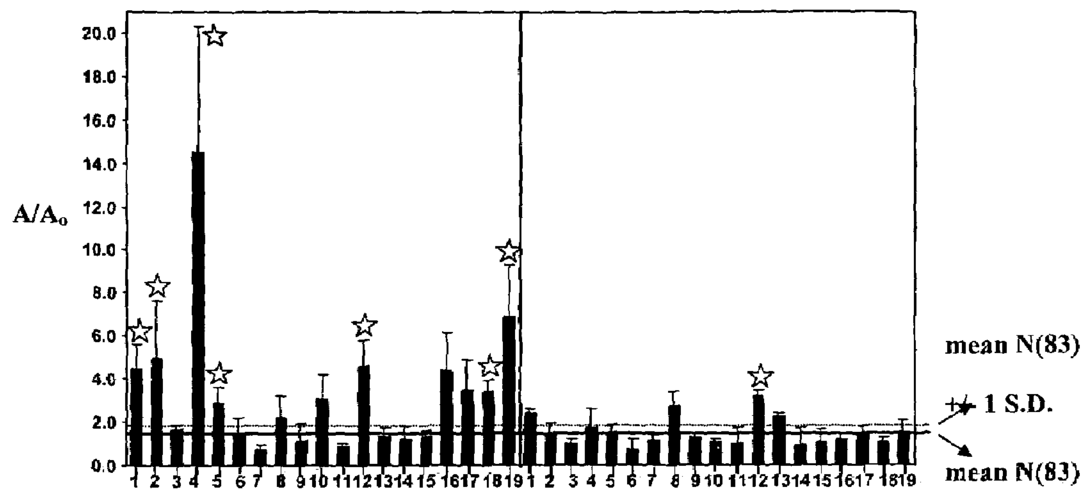

FIG. 11. ELISA of anti-CEP IgG autoantibodies in human plasma. Each bar represents the mean value +/−S.D. of at least 3 independent studies. The horizontal solid line represents the mean value for the N(83) cohort. The dashed line represents the mean value of the N (83) cohort plus 1 S.D. Bars marked with stars indicate that 7 AMD plasmas consistently exhibit high antiCEP IgG reactivity in both ELISA and dot-blot (data not shown) analyses, whereas, only 1 control exhibited high antiCEP IgG reactivity in both analyses.

FIG. 12. Structures of 2-(ω-carboxyethyl)pyrrole, CEP (top), and 2-(ω-carboxypropyl)pyrrole, CPP (bottom).

Figure 13:
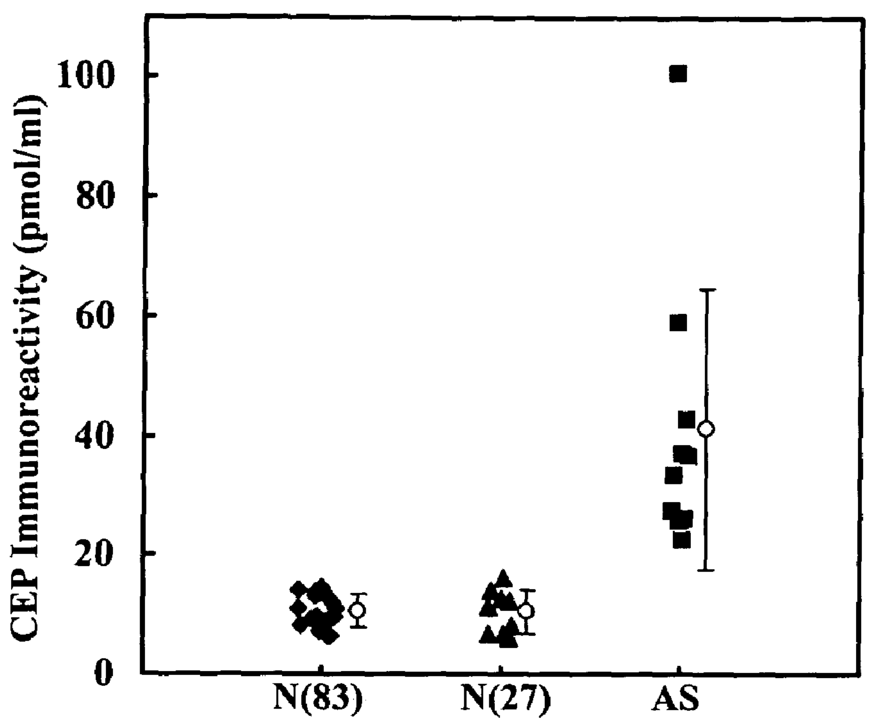

FIG. 13. Levels of CEP adduct immunoreactivity detected in human plasma from (♦) 83 aged normal volunteers, (σ) 27 normal young healthy volunteers, and (v) 10 patients who were diagnosed to have atherosclerosis (AS). The figure also shows mean levels detected (O). The error bars indicate the standard deviation (S.D.) for data set.

Figure 14:
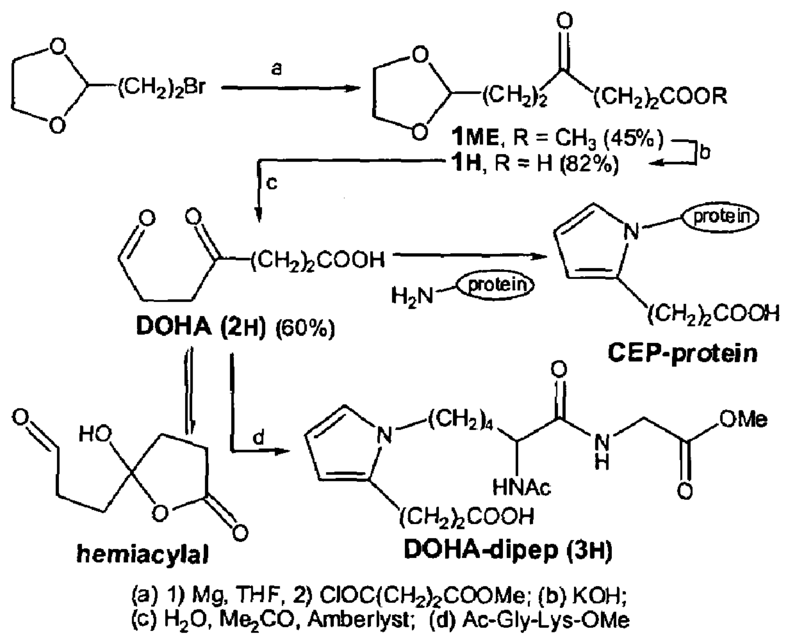

FIG. 14. Synthesis of Protein and Peptide Derivatives of DOHA.

DETAILED DESCRIPTION OF THE INVENTION

Diagnostic methods for identifying test subjects who have or are at risk of developing age-related macular degeneration, atherosclerosis, or an analogous disease which involves oxidative damage to tissues from oxidation of docosahexaenoic acid (DHA) containing lipids are provided. The methods are based, at least in part, on the discovery that patients diagnosed with AMD or atherosclerosis have higher levels of CEP adducts in their blood than normal control subjects. The present methods are also based, at least in part, on the discovery that patients diagnosed with AMD have higher levels of anti-CEP antibodies in their blood than normal healthy subjects.

In one aspect, the methods comprise assaying for the presence of elevated levels of CEP adduct in a bodily fluid taken from the test subject. Preferably, the assay employs an antibody which is immunospecific for the CEP adduct. In another aspect, the methods comprise assaying for the presence of elevated levels of antibodies which are immunospecific for CEP adducts in a bodily fluid obtained from the test subject. Advantageously, the present methods are minimally invasive and provide an objective and quantifiable index of ongoing DHA oxidative damage in a test subject.

The present invention also relates to kits and reagents for diagnosing diseases which involve oxidative damage to tissues from oxidation of docosahexaenoic acid (DHA)-containing lipids.

I. Determining the Levels of CEP Adducts in Bodily Fluids of the Test Subject The bodily fluids which may be obtained from the subject and used as test samples in the present diagnostic methods include blood, serum, plasma, spinal fluid, ocular fluid, and tears. The preferred samples are blood, serum, and plasma. Preferably, an antioxidant and a protease inhibitor are added to the test sample immediately after the bodily fluid is obtained from the subject to prevent spurious oxidation of DHA-containing lipids or proteolysis of CEP-containing proteins in the test sample. In those cases where the test sample is to be stored prior to analysis it is preferred that the sample containing the antioxidant and protease inhibitor is quench frozen and stored at approximately −80° C.

Preferably, the presence of the CEP adduct in the bodily fluid is detected using an antibody that is immuno-specific for CEP adducts. The term "immuno-specific" means the antibodies have at least 100 times greater affinity for a CEP adduct than for other 2-(ω-carboxyalkyl)pyrrole (CAP) adducts, including 2-(ω-carboxypropyl)pyrrole. (CPP) adducts. Such antibodies include, but are not limited to, polyclonal, monoclonal, chimeric, single chain, and Fab fragments. Optionally, the diagnosis is made by comparing the amount, concentration or content of CEP in a sample obtained from the test subject to the titer of CEP in samples obtained from subjects lacking the disease, i.e., healthy or normal subjects. Alternatively, the amount, concentration or content of CEP in the sample may be compared to the amount, concentration or content in corresponding samples which were taken from the test subject for the purpose of determining baseline concentrations of the CEP, such as for example during an early screening procedure.

Since the bodily fluids of test subjects contain elevated levels of both the free acid form of CEP adducts, which are detectable with anti-CEP antibodies, and ester forms of the CEP adducts (e.g., esters of PC), which are normally not detectable with anti-CEP antibodies, the bodily fluids may be treated with a base (e.g. KOH) prior to contacting the test sample with the anti-CEP antibody. Such treatment converts CEP esters to CEP free acids, making it possible to detect total alterations in the levels of all CEP adducts in the bodily fluid of the test subject, including those present in the form of esters.

Methods of Determining Levels of CEP Adducts in a Bodily Fluid Obtained from the Test Subject.

The levels of CEP adducts in a bodily fluid obtained from the test subject can be determined using polyclonal or monoclonal antibodies that are reactive with a CEP adduct. Anti-CEP-antibodies may be made and labeled using standard procedures and then employed in immunoassays to detect the presence of phospholipid-bound, amino acid-bound, peptide-bound or protein-bound CEP in the sample. Suitable immunoassays include, by way of example, radioimmunoassays, both solid and liquid phase, fluorescence-linked assays or enzyme-linked immunosorbent assays and Western blot analysis. Optionally, the immunoassays are also used to quantify the amount of CEP adducts that are present in the sample.

Antibodies raised against CEP adducts for use in such immunoassays are produced by conjugating CEP to a carrier protein or generating CEP by modification of a carrier protein with a dioxo fatty acid and then using the adduct to immunize a host animal. Suitable host animals, include, but are not limited to, rabbits, mice, rats, goats, and guinea pigs. Various adjuvants may be used to increase the immunological response in the host animal. The adjuvant used depends, at least in part, on the host species. For example, guinea pig albumin is commonly used as a carrier for immunizations in guinea pigs. Such animals produce heterogenous populations of antibody molecules, which are referred to as polyclonal antibodies and which may be derived from the sera of the immunized animals.

Monoclonal antibodies, which are homogenous populations of an antibody that binds to a particular antigen, are obtained from continuous cells lines. Conventional techniques for producing monoclonal antibodies are the hybridoma technique of Kohler and Millstein (Nature 356:495–497 (1975)) and the human B-cell hybridoma technique of Kosbor et al (Immunology Today 4:72 (1983)). Such antibodies may be of any immunoglobulin class including IgG, IgM, IgE, IgA, IgD and any class thereof. To increase the likelihood that monoclonal antibodies specific to the CEP are produced, the CEP may be conjugated to a carrier protein which is present in the animal immunized.

Methods of Determining the Levels of Anti-CEP Antibodies in a Bodily Fluid Obtained from the Test Subject.

The present invention also provides diagnostic methods which involve determining the levels of anti-CEP antibodies in a bodily fluid from the subject. The method comprises the steps of contacting the bodily fluid with a CEP peptide or protein adduct, and assaying for the formation of a complex between the CEP peptide or protein adduct and antibodies in the sample. For ease of detection, it is preferred that the CEP peptide or protein adduct be attached to a substrate such as a column, plastic dish, matrix, or membrane, such as nitrocellulose or polyvinyl difluoride (PVDF). The sample may be untreated, subjected to precipitation, fractionation, separation, or purification before combining with the CEP peptide or protein adduct. Interactions between antibodies in the sample and the CEP peptide or protein adduct are detected by radiometric, colorimetric, or fluorometric means, size-separation, or precipitation. Preferably, detection of the antibody-CEP peptide or protein adduct complex is by addition of a secondary antibody that is coupled to a detectable tag, such as for example, an enzyme, fluorophore, or chromophore. Formation of the complex is indicative of the presence of anti-CEP antibodies, either IgM or IgG, in the test sample.

Preferably, the method employs an enzyme-linked immunosorbent assay (ELISA) or a Western immunoblot procedure. Such methods are relatively simple to perform and do not require special equipment as long as membrane strips are coated with a high quality antigen Comparison of Levels of CEP Adducts or Anti-CEP Antibodies in Bodily Fluids Obtaind from a Test Subject to Predetermined Values.

The levels of each diagnostic marker, i.e., the CEP adducts and the anti-CEP antibodies, in the test subject's bodily fluid may be compared to a single predetermined value or to a range of predetermined values. If the level of the present diagnostic marker in the test subject's bodily fluid is greater than the predetermined value or range of predetermined values, the test subject has or is at greater risk of developing or having a disease associated with oxidation of DHA-containing lipids, e.g. AMD or atherosclerosis, than individuals with levels comparable to or below the predetermined value or predetermined range of values. The extent of the difference between the level of the diagnostic marker in the bodily fluid obtained from the test subject and the predetermined value is also useful for characterizing the extent of the disease or risk of developing the disease and thereby, determining which individuals would most greatly benefit from certain aggressive therapies. The present diagnostic tests are useful for determining if and when therapeutic agents which are targeted at preventing AMD or atherosclerosis should and should not be prescribed for a patient.

Evaluation of Therapeutic Agents Targeted at AMD or Atherosclerosis

The present diagnostic tests are also useful for evaluating the effect of therapeutic agents targeted at AMD or atherosclerosis on patients who have been diagnosed as having or being at risk of developing AMD or atherosclerosis. Such evaluation comprises determining the levels of one or more of the present diagnostic markers including CEP adducts, anti-CEP antibodies and combinations thereof, in a bodily fluid taken from the subject prior to administration of the therapeutic agent and a corresponding bodily fluid taken from the subject following administration of the therapeutic agent. A decrease in the level of the selected diagnostic marker in the sample taken after administration of the therapeutic as compared to the level of the selected diagnostic marker in the sample taken before administration of the therapeutic agent is indicative of a positive effect of the therapeutic agent on AMD or atherosclerosis in the subject.

II. Diagnostic Kits

Diagnostic kits and reagents which may be employed in assays to detect the presence of a CEP adduct in bodily samples of test subjects are provided. The diagnostic kit comprises an antibody, preferably a monoclonal antibody, which is used in an immunoassay to detect the presence or quantify the amount of CEP adduct present in a sample. Preferably, the diagnostic kit further comprises a CEP adduct such as, for example, an adduct in which the CEP adduct is conjugated to a protein or peptide. Such adduct may be employed to generate a standard curve for quantification or as a competitor to demonstrate antibody specificity.

EXAMPLES

The following examples are for purposes of illustration only and are not intended to limit the scope of the claims which are appended hereto. All references cited herein are specifically incorporated herein by reference.

Abbreviations:

AA, arachidonic acid; AA-PC, 2-arachidonylphosphatidylcholine; Ac-Gly-Lys-OMe, methyl 6-amino-2-((acetylamino)acetyl)amino)hexanoate; BCA, bicinchoninic acid; BHT, butylated hydroxytoluene; BRB, blood-retinal barrier; BSA, bovine serum albumin; CAP, 2-(carboxyalkyl)pyrrole; CEO, chicken egg ovalbumin; CEP, 2-(ω-carboxyethyl)

pyrrole; CHP, 2-(ω-carboxyheptyl)pyrrole; CPP, 2-(ω-carboxypropyl)pyrrole; DHA, docosahexaenoic acid; DODA, 9,12-dioxododecanoic acid; DOHA, 4,7-dioxoheptanoic acid; DOHA-dipep, 8-(1-(5-((acetylamino)acetyl)amino)-5-(methoxycarbonyl)pentyl)pyrrol-2-yl)hexanoic acid; DOOA, 5,8-dioxooctanoic acid; EDTA, ethylenediaminetetraacetate; EI, electron ionization; ELISA, enzyme-linked immunosorbent assay; HNE, (E)-4-hydroxy-2-nonenal; HODA, 9-hydroxy-12-oxo-10-dodecenoic acid; HOHA, (E)-4-hydroxy-7-oxohept-5-enoic acid; HOOA, 5-hydroxy-8-oxo-6-octenoic acid; HRMS, high resolution mass spectrum; HSA, human serum albumin; IgG, immunoglobin G; KLH, keyhole limpet hemocyanin; LA, linoleic acid; LA-PC, 2-linoleylphosphatidylcholine; LDL, low density lipoprotein; LSC, liquid scintillation counting; MDA, malondialdehyde; m/z, mass to charge ratio; NMR, nuclear magnetic resonance; ON, 4-oxononanal; PBS, phosphate buffered saline; PC, phosphatidylcholine; $PLA_2$, phospholipase $A_2$; PP-ACA, 2-pentylpyrrolated 6-aminocaproic acid; PUFA, polyunsaturated fatty acid; $R_f$, retention factor; ROS, rod outer segment; RPE, retinal pigment epithelium; TBDMSCl, t-butyl(dimethyl)silyl chloride; THF, tetrahydrofuran; TLC, thin layer chromatography.

Oxidation of Polyunsaturated Fatty Acids

Figure 1:
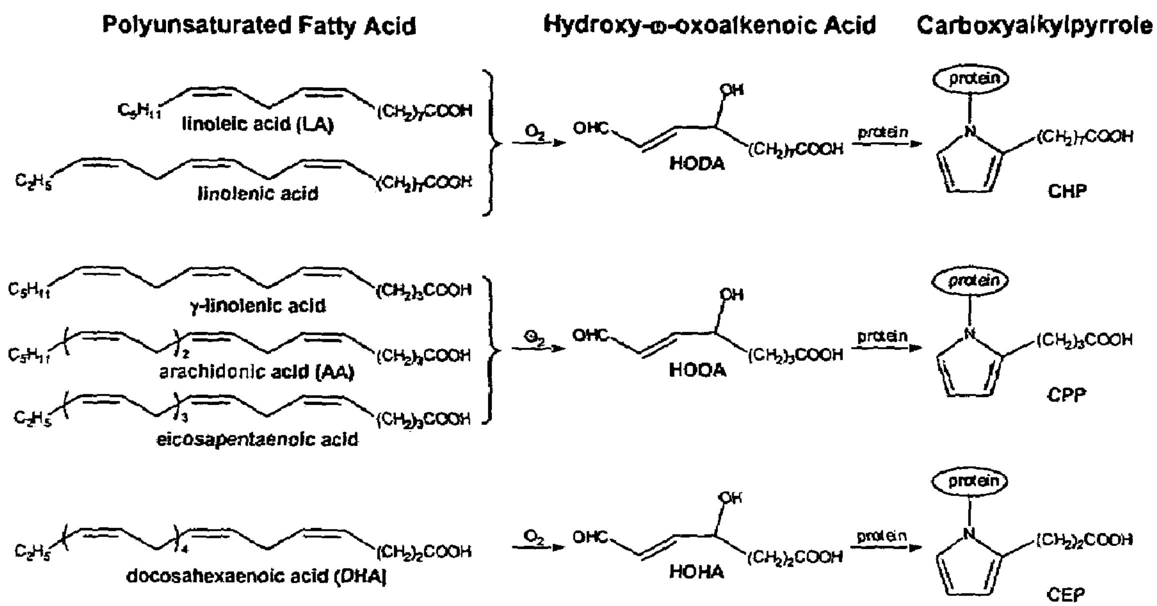
FIG. 1. Generation of 2-(ω-carboxyalkyl)pyrrole epitopes.
Figure 2:
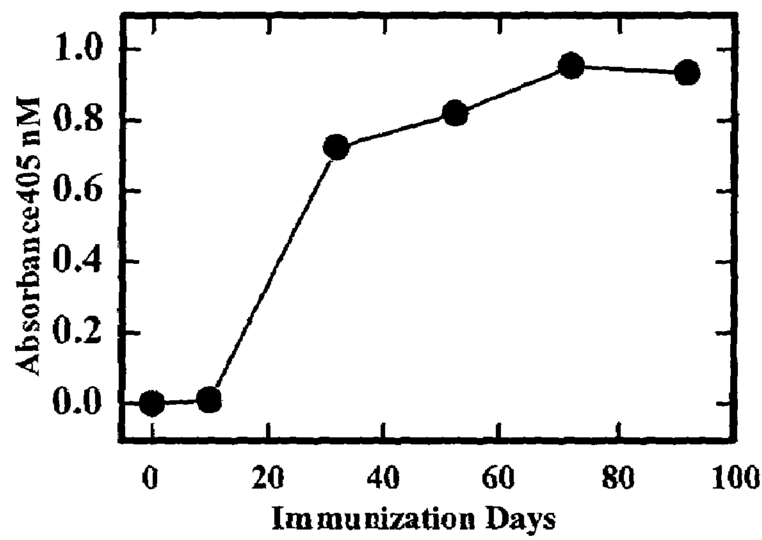
FIG. 2. Serum anti-CEP antibody titer (λ) in New Zealand white rabbit immunized with CEP-KLH using CEP-BSA as coating agent.

We recently showed that oxidation of polyunsaturated fatty acids (PUFAs) in the presence of protein leads to the generation of 2-(ω-carboxyalkyl)pyrrole (CAP) epitopes (FIG. 1) (Fliesler, S. J. and Anderson, R. E., (1983) Chemistry and metabolism of lipids in the vertebrate retina, *Prog. Lipid Res.* 22 79–131). Thus, oxidative fragmentation of arachidonic acid (AA) or linoleic acid (LA) produces 5-hydroxy-8-oxooct-6-enoic acid (HOOA) or 9-hydroxy-12-oxododec-10-enoic acid (HODA), respectively, and these products are capable of reacting with protein to generate protein-bound 2-(ω-carboxypropyl)pyrrole (CPPs) or 2-(ω-carboxyheptyl)pyrroles (CHPs). Oxidative fragmentation of several other common PUFAs can also produce CHPs and CPPs. In contrast, only one common PUFA, DHA, is expected to give rise to CEPs by oxidative cleavage to HOHA (see FIG. 1). Tissues rich in DHA-containing lipids include the retina and certain regions of the brain. DHA lipids are found at significantly lower levels in blood plasma and most other tissues.

To selectively detect the occurrence of CEP adducts in vivo using immunological tools, it is highly desirable to raise antibodies that can distinguish between CEP adducts and CPP adducts, adducts that differ by only one $CH_2$, group. As indicated below, we have determined that (i) remarkably high structural discrimination can be achieved with rabbit polyclonal antibodies, (ii) both oxidation of a DHA phospholipid in the presence of protein and reaction of a synthetic phospholipid ester of HOHA with protein generates CEP esters, and (iii) CEP immuno-reactivity is abundant in DHA-rich regions of the retina.

Example 1

Peptide and Protein-Based CEPs and Rabbit Anti-CEP Antibody

A. Methods

Methyl 6-(2,5-Dioxolanyl)-4-oxohexanoate (1Me). A solution of 2-(2-bromoethyl)-1,3-dioxolane (4.37 g, 24 mmol) in anhydrous tetrahydrofuran (THF, 25 ml) was added dropwise over 1.5 h to Mg turnings (0.6 g, 24.7 mmol) under argon, while maintaining the temperature below 35° C. (Boga, C., Savoia, D., Trombini, C. and Umani-Ronchi, A. (1986), A short route to 2-(6-methoxycarbonylhexyl) cycoplent-2-en-1-one, *Synthesis,* 212–213). The reaction mixture was then left at room temperature overnight. The Grignard reaction mixture was cooled to −78° C., and 3-carbomethoxypropionyl chloride (3.1 g, 20.5 mmol) dissolved dry THF (20 mL) was added dropwise over 1 h. The resulting mixture was then stirred for 20 min, quenched with a saturated aqueous solution of $NH_4Cl$ (50 mL), and extracted with EtOAc (4×50 mL). The combined organic phase was washed with brine, dried with $MgSO_4$, and evaporated to obtain the crude product. The crude compound was purified by silica gel chromatography (EtOAc/hexane, 3:7, v/v, as eluant) to yield 2.3 g (45%) of pure keto ester 1Me. $^1H$ NMR (200 MHz, $CDCl_3$). δ 4.91 (t, J=4.3 Hz, 1H), 3.83–3.96 (m, 4H), 3.73 (s, 3H), 2.75 2H), 2.59 (m, 4H); 1.98 (m, 2H); $^{13}C$ NMR ($CDCl_3$) δ 208.02 (CO), 173.29 (CO), 103.22 (CH), 65.00 ($CH_2$), 51.82 ($CH_3$), 37.03 ($CH_2$), 36.44 ($CH_2$), 27.74 ($CH_2$), 27.53 ($CH_2$). HRMS (EI) (m/z) calcd for $C_{10}H_{15}O_5$ ($M^+$-H) 215.0996. found 215.0919.

6-(2,5-Dioxolanyl)-4-oxohexanoic Acid (1H). Ester 1Me (396.5 mg, 1.8 mmol) in 10 mL of $H_2O$/MeOH/THF (2:5:3, v/v/v) was stirred for 1.5 h with NaOH (366.7 mg, 9.2 mmol) at room temperature (Kaur, K. Salomon, R. G., O'Neil, J. and Hoff, H. F. (1997) (Carboxyalkyl)pyrroles in human plasma and oxidized low-density lipoproteins, *Chem Res. Toxicol* 10, 1387–1396). The reaction mixture was then acidified to pH 3.0 and extracted with EtOAc (3×25 mL). The combined organic phase was washed with $H_2O$, and then EtOAc was concentrated by rotary evaporation to give acid acetal 1H (304 mg, 82%). $^1H$ NMR (200 MHz, $CDCl_3$) δ 4.91 (t, J=4.2 Hz, 1H), 3.80–3.99 (m, 4H), 2.62–2.74 (m, 4H), 2.58 (t, J=7.4 Hz, 2H); 1.99 (q, J=7.4 Hz, 4.2 Hz, 2H); $^{13}C$ NMR ($CDCl_3$) δ 208.02 (CO), 178.47 (CO), 103.18 (CH), 64.98 ($CH_2$), 36.78 ($CH_2$), 36.35 ($CH_2$), 27.81 ($CH_2$), 27.48 ($CH_2$). HRMS (EI) (m/z) calcd for $C_9H_{14}O5$ ($M^+$) 202.0814. found 202.0868. calcd for $C_9H_{13}O_4$ ($M^+$-OH) 185. 0814. found 185.0818.

4,7-Dioxoheptanoic Acid (DOHA, 2H). The acid acetal 1H (304 mg, 1.5 mmol) was stirred in acetone (55 mL) and $H_2O$ (3–5 drops) with Amberlyst catalyst (2.3 g) at room temperature for 5 h (Rees, M. S., van Kuijk, F. G. J. M., Siakotos, A. N. and Mundy, B. P., (1995) Improved synthesis of various isotope labeled 4-hydroxyalkenals and peroxidation intermediates, *Synth. Commun.* 25, 3225–3236). The reaction mixture was filtered through a bed of anhydrous $MgSO_4$. The solvent was removed by rotary evaporation to obtain the keto aldehyde 2H (220 mg) that was used without further purification to prepare carboxyethyl pyrroles. $^1H$ NMR ($CDCl_3$) δ 2.43 (m, 4H), 2.77 (m, 4H), 9.70 and 9.60 (1H) $^{13}C$ NMR ($CDCl_3$) 208.31 (CO), 202.02 (CO), 173.82 (CO), 36.62 ($CH_2$), 36.54 ($CH_2$), 34.38 ($CH_2$), 27.41 ($CH_2$). DOHA (2H) was characterized further by conversion into a pyrrole derivative, DOHA-dipep (3H, vide infra).

8-(1-(5-((2-(Acetylamino)acetyl)amino)-5-(methoxycarbonyl)pentyl)pyrrol-2-yl)hexanoic Acid (DOHA-dipep, 3H). DOHA (2 mg, 0.01 mmol) and methyl 6-amino-2-((2-acetylamino)acetyl)amino)hexanoate (Ac-Gly-Lys-OMe, 3.7 mg, 0.012 mmol) dissolved in MeOH (0.3 mL) were stirred for 48 h under nitrogen at room temperature. Solvents were then removed by evaporation into a dry ice-cooled trap using high vacuum. The crude product was purified by chromatography on silica gel with $CHCl_3$/MeOH (9:1, v/v) as eluant to deliver the title CEP derivative DOHA-dipep (3H): $^1$H NMR ($CD_3OD$) δ 1.36 (m, 2H), 1.72 (m, 2H), 1.86 (m, 2H), 2.06 (s, 3H), 2.59 (t, J=7.4, 2H), 2.75 (t, J=7.8, 2H), 3.70 (s, 3H), 3.89 (m, 4H), 4.41 (m, 1H), 5.80 (m, 1H), 5.93 (m, 1H), 6.58 (m, 1H); HRMS calcd for $C_{18}H_{27}N_3O_6$ ($M^+$) 381.1900. found 381.1895.

CEP-KLH Antigen. DOHA (2H, 2.4 mg) and KLH (4.67 mg) in 0.5 M pH 7.4 sodium phosphate buffer (1 mL) was incubated at room temperature under argon for 4 days followed by three successive 12 h dialyses against 10 mM pH 7.4 sodium phosphate buffer (3×1 L). The final protein concentration (2.72 mg/mL) was determined using the Pierce bicinchoninic acid (BCA) protein reagent (Smith, P. K., Krohn, R. I., Hermanson, G. T., Mallia, A. K., Gartner, F. H., Provenzano, M. D., Fujimoto, E. K., Goeke, N. M., Olson, B. J. and Klenk, D.C. (1985) Measurements of protein using bicinchoninic acid. *Anal. Biochem.* 150, 76–85). Thus, a series of standard solutions of BSA (0.2, 0.4, 0.6, 0.8, 1.0, and 1.2 mg/mL) were prepared. One-tenth and one-fifth dilutions (100 μL each) of sample (CEP-KLH) were prepared. Equal volumes (2000 μL) of BCA protein assay solution were added to the standards (100 μL) and samples (100 μL). The resulting mixtures were then vortexed and incubated at 37° C. for 2 h. The pyrrole concentration (46 μM) was determined using Ehrlich reagent, 4-(dimethylamino)benzaldehyde, as described previously (15) using DOHA-dipep (3H) as a standard.

CEP-HSA. A solution of DOHA (2H, 56 mg, containing about 50% of the ω-ketoaldehyde form) and HSA (0.08 mM), final concentration, in 7 mL of 0.5 M pH 7.4 sodium phosphate buffer was incubated at room temperature under argon for 10 days, and then dialyzed twice (24 h each) against 1 L of 10 mM sodium phosphate buffer (pH 7.4). The final protein concentration determined using Pierce BCA protein assay, as described above, was 3.8 mg/mL. The pyrrole concentration (87 μM) was determined using Ehrlich reagent, 4-(dimethylamino)benzaldehyde, as described previously (DeCaprio, A. P., Jackowshi, S. J. and Regan, K. A., (1987) Mechanism of formation and quantitation of imines, pyrroles, and stable nonpyrrole adducts in 2,5-hexanedione-treated protein, *Mol. Pharmacol.* 32, 542–548) using DOHA-dipep (3H) as a standard. This corresponds to a pyrrole:HSA ratio of 1.5:1. The presence of lysine-based CEP in CEP-HSA, the DOHA adduct of HSA, was demonstrated by nanoelectrospray mass spectrometry and MS/MS analysis of tryptic peptides.

Tryptic Digestion of CEP-HSA. CEP-HSA (3.8 mg/mL) was diluted to 1 mg/mL with water. Urea and ammonium bicarbonate were added to make the final concentrations 8 M for Urea, and 400 mM for ammonium bicarbonate. Reduction of disulfide bonds was achieved by treatment with DTT (10 mM final concentration). After 30 min at room temperature, the thiol groups were alkylated by the addition of iodoacetamide (50 mM final concentration) and incubation for an additional 30 min at room temperature. After dialysis against 10 mM ammonium bicarbonate (4×500 mL) for 24 hours, 20 μL of this sample (0.87 mg/mL) was then digested at 37° C. with modified trypsin (Promega), added in 2 equal portions (0.1 μg per addition) at 12 h intervals.

MALDI-TOF Mass Spectrometric Analysis of CEP-HSA Tryptic Peptides. MALDI-TOF analysis was done using a PE Biosystems Voyager DE Pro instrument equipped with a nitrogen laser (337 nm) and operated in the delayed extraction and reflector mode with a matrix of ω-cyano-4-hydroxycinnamic acid (5 mg/mL in acetonitrile/water/3% trifluoroacetic acid, 5:4:1, v/v/v). Internal standards were used for calibration, which included two synthetic peptides, G91 (MH+ 1015.579) and L20R (MH+ 2474.630). One μL of sample was mixed with 1 μL of matrix and 0.5 μL of internal standard mixture. Two μL of the resulting mixture was applied to the sample plate and allowed to dry. Each spectrum was accumulated for ~250 laser shots. Measured peptide masses were used to search the Swiss Prot, TrEMBL or NCBI sequence databases for protein identification. Using MS-Fit (http://prospector.ucsf.edu/htmlucsf3.0/ms-fit.htm), the peptide map dataset was searched with a mass tolerance of 0.005% error (=50 ppm).

Characterization of CEP Modified Tryptic Peptides. Peptides with putative CEP modifications were analyzed by tandem nanoelectrospray MS/MS spectrometry, using a PE Sciex API 3000 triple quadrupole electrospray instrument fitted with a nanospray interface (Protana). Tryptic digests were eluted from Zip Tips (Millipore) in 80% acetonitrile/20% water containing 0.02% trifluoroacetic acid, and 5 μL samples were infused at 50 nL/min through gold coated glass capillaries (2 μm id, New Objectives, Inc). Low energy collision MS/MS was performed with 1000–1500 V applied to the capillary, an orifice potential of 40 V, nitrogen as the collision gas, CAD gas at ~$2.1\times10^{15}$ molecules/cm$^2$, and 80 scans were accumulated. Spectra were acquired in positive ion mode using a step size of 0.2 Da and 0.5 ms dwell time. The Q1 resolution was lowered to allow transmission of M+1 isotopic precursor ions into Q2; Q3 was kept at unit mass resolution.

CEP-BSA. A solution of DOHA (2H, 16 mg) and BSA (0.08 mM), final concentration, in 0.5 M pH 7.4 sodium phosphate buffer (5 mL) was incubated at room temperature under argon for 10 days and then dialyzed twice (24 h each) against 10 mM pH 7.4 sodium phosphate buffer (2×1 L). The final protein concentration determined using Pierce BCA protein assay, as described above, was 4.3 mg/mL. The pyrrole concentration (93 μM) was determined using Ehrlich reagent, 4-(dimethylamino)benzaldehyde, as described previously (15) using DOHA-dipep as a standard. This corresponds to a pyrrole:BSA ratio of 1.4:1.

CEP-GPDH. A solution of DOHA (2H, 30 mg) and GPDH (0.1 mM) in 5 mL of 0.5 M pH 7.4 PBS was incubated at room temperature PBS (pH 7.4). The final protein concentration determined using Pierce BCA protein assay, as described above, was 2.8 μg/ml. The pyrrole concentration (88 μM) was determined using Ehrlich reagent, 4-(dimethylamino)benaldehyde, as described previously (DeCaprio, A. P., Jackowshi, S. J. and Regan, K. A., (1987) Mechanism of formation and quantitation of imines, pyrroles, and stable nonpyrrole adducts in 2,5-hexanedione-treated protein, *Mol. Pharmacol.* 32, 542–548) using DOHA-dipep as a standard. This corresponds to a pyrrole:GPDH ratio of 1.1:1.

Immunization. The immunogen, CEP-KLH (0.02 μmol of pyrrole groups/mg of KLH, 2.72 mg/mL KLH in pH 7.4 PBS), was emulsified in Freund's complete adjuvant (400 μL). One Pasturella-free, New Zealand white rabbit was inoculated intradermally into several sites on the back (125 μL) and rear legs (125 μL). Booster injections were given every 21 days. Antibody titers were monitored 10 days after each inoculation by enzyme-linked immunosorbent assay (ELISA) as described below.

Antibody Purification: Protein G Column. The crude anti-CEP-KLH antibody serum from the 92 day bleeding of the rabbit contained 18.8 mg/mL protein as determined by absorbance ($A_{280}$=1.35 mg/mL) at 280 nm (Harlow, E. and Lane, D. (1988) *Antibodies: a laboratory mannual*, Cold Spring Harbor Laboratory, Cold Spring Harbor, N.Y.). A column was packed with 1.0 mL of immunopure (G) immobilized protein G gel and was equilibrated with 5 column volumes of immunopure (G) IgG binding buffer. Binding buffer (pH 5.0, 1 mL) was added to the above crude antibody serum (1.0 mL) and the mixture was vortexed for 1 min. Then it was centrifuged for 20 min at 3000 rpm (1900 g), and the supernatant was applied to the equilibrated column. The sample was allowed to flow completely into the gel, and 6–10 column volumes of the binding buffer were passed through the column until the $A_{280}$ of the effluent approached baseline to remove the unbound serum (non-IgG proteins). The bound IgG was then eluted with immunopure IgG elution buffer (pH 2.6) and was collected into 1.0 mL fractions. The higher absorbance fractions were combined and dialyzed against pH 7.4 PBS (2×2 L) at 4° C. for 24 h. The resulting solution of anti-CEP-KLH (4 mL) contained 0.30 mg/mL purified IgG, as determined by absorbance at 280 nm.

Antibody Titer. To determine anti-CEP-KLH antibody level in rabbit blood serum, the BSA conjugate (CEP-BSA, containing 1.2:1 pyrrole:protein molar ratio) was used as coating agent. The CEP-BSA (100 μL of solution containing 8.6 μg/mL in pH 7.4 PBS) was added to each well of a sterilized Baxter ELISA plate. The plate was then incubated at 37° C. for 1 h in a moist chamber. The coating solution was discarded. Each well was washed with PBS (3×300 μL), then filled with 1.0% chicken egg ovalbumin (CEO) in PBS (300 μL), and incubated at 37° C. for 1 h to block remaining active sites on the plastic phase. Each well was then washed with 0.1% CEO in PBS (300 μL). Then rabbit serum from each bleeding (100 μL) diluted 1:10000 with 0.2% CEO in PBS, or 0.2% CEO in PBS without serum for a black, was dispensed into the sample wells. Normal rabbit (not injected with antigen) serum diluted as above was employed as a negative response control. The remaining ELISA was done as described previously for similar studies with anti-CPP-KLH (DOOH-KLH) and anti-CHP-KLH (DODA-KLH) antibodies (Kaur, K., Salomon, R. G., O'Neil, J. and Hoff, H. F. (1997) (Carboxyalkyl)pyrroles in human plasma and oxidized low-density lipoproteins. *Chem Res Toxicol* 10 1387–96.). The anti-CEP antibody titer rose rapidly after the second inoculation plateauing after 30 days. The rabbit was exsanguinated after 92 days and a total of 5 inoculations.

Figure 3:
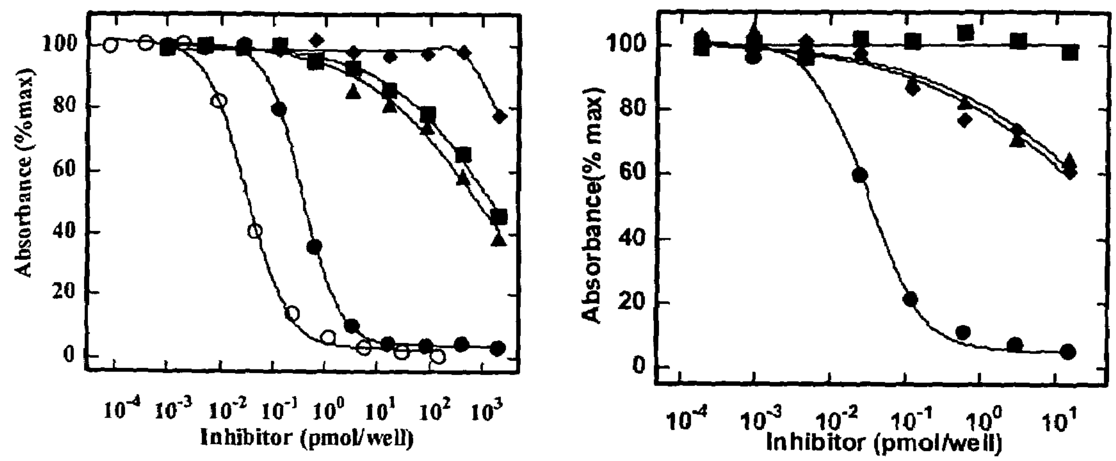
FIG. 3. (A) Inhibition curve for binding of anti-CEP-KLH to CEP-BSA by CEP-HSA (λ), CPP-HSA (♦), CHP-HSA (σ), PP-ACA-BSA (ν), and HSA (Δ). (B) Inhibition curve for binding of anti-CEP-KLH to CEP-BSA by CEP-HSA (O) and for binding of anti-CEP-KLH to CEP-GPDH by CEP-HSA (λ), CPP-HSA (σ), CHP-HSA (ν), PP-ACA-BSA (♦) and GPDH (Δ).
Figure 4:
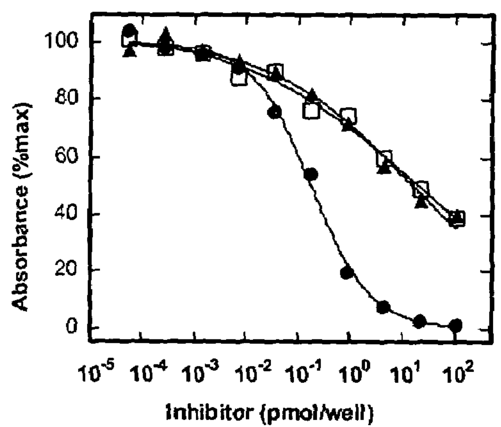
FIG. 4. Inhibition curves for binding of anti-CPP-KLH to CPP-BSA by CPP-HSA (●), CEP-HSA (♦), CHP-HSA (□)

Competitive Antibody Binding Inhibition Studies. For antibody binding inhibition studies to measure cross-reactivities, CEP-BSA, CEP-GDPH and CPP-BSA were used as coating agents and CEP-HSA and CPP-HSA were used as standards for purified anti-CPP-KLH and anti-CPP-KLH, respectively. The ELISAs were done as described previously for studies with anti-CPP-KLH (DOOH-KLH) antibodies (Kaur, K., Salomon, R. G., O'Neil, J. and Hoff, H. F. (1997) (Carboxyalkyl)pyrroles in human plasma and oxidized low-density lipoproteins. *Chem Res Toxicol* 10 1387–96.). Typical inhibition curves are presented in FIGS. 3 and 4.

B. Results

Synthesis of ω-Carboxyethylpyrrolated Protein and Peptide Derivatives. Paal-Knorr reactions of μ-dicarbonyl compounds with primary amines provides an efficient route to 2-(ω-carboxyalkyl)pyrroles (Kaur, K., Salomon, R. G., O'Neil, J. and Hoff, H. F. (1997) (Carboxyalkyl)pyrroles in human plasma and oxidized low-density lipoproteins. *Chem Res Toxicol* 10 1387–96.). (See FIG. 14). To generate the requisite 2-(ω-carboxyethyl)pyrroles by this chemistry, a synthesis of the ω-ketoaldehyde DOHA (2H) was developed that exploits the selective reaction with acyl halides of the Grignard reagent produced from 2-(2-bromoethyl)-1,3-dioxolane. Acylation of this organomagnesium derivative with 3-carbomethoxypropionyl chloride delivered ketoester 1ME. Hydrolysis of the ethylene ketal in the derived keto acid 1H produced a mixture containing the requisite ω-ketoaldehyde DOHA (2H), presumably in equilibrium with the corresponding hemiacylal because the $^{1}$H NMR exhibits two aldehydic hydrogen singlets. Paal-Knorr condensation of this DOHA preparation with the dipeptide Ac-Gly-Lys-OMe provided the carboxyethylpyrrole, DOHA-dipep (3H), that was fully characterized by $^{1}$H NMR spectroscopy and high resolution mass spectrometry. Similar reaction of keyhole limpet hemocyanin (KLH), BSA, GPDH, or HSA delivered carboxyethylpyrrolated (CEP) proteins CEP-KLH, CEP-BSA, CEP-GPDH, or CEP-HSA respectively.

Figure 5:
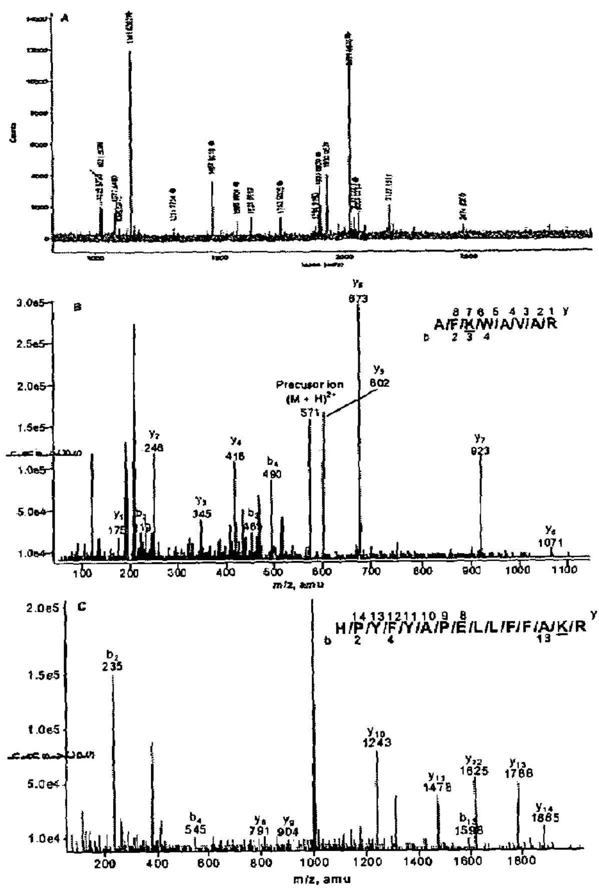
FIG. 5. Characterization of CEP-HSA by MALDI-TOF and tandem MS. (A) MALDI-TOF mass spectrum of tryptic digest of CEP-HSA. Arrows denote internal standards. Dots denote tryptic peptides from HSA identified by a "MS-Fit" sequence database search. Asterisks denote possible CEP modified peptides based on the sum of the adduct mass (122.0366) and the mass of the peptide. (B) Nanoelectrospray MS/MS spectrum of the doubly charged ion m/z 571 (from singly charged m/z 1141.6302 in panel A). (C) Nanoelectrospray MS/MS spectrum of the doubly charged ion m/z 1101 (from singly charged m/z 2021.0678 in panel A).

Mass Spectroscopic Characterization of CEP-HSA. Confirmation that CEP-protein adducts contain carboxyethylpyrrolated lysyl residues was accomplished by mass spectroscopic analysis of tryptic peptides (FIG. 5). Two peptides from CEP-HSA were identified by MALDI-TOF mass spectroscopy, m/z 1141.6302 and m/z 2021.0678, that are apparently CEP derivatives (FIG. 5, panel A). The nanoelectrospray MS/MS spectrum of the m/z 1141 peptide exhibited a series of fragment ions that allow unambiguous identification of a CEP modification on the HSA lysine residue K236 (FIG. 5, panel B). The MS/MS spectrum of the m/z 2021 peptide (FIG. 5, panel C), that contains lysine residue K183, was also consistent with a CEP modification.

Antibody Specificity. The structural specificities of anti-CEP-KLH and anti-CPP-KLH antibodies were compared and contrasted (Table 2). The CEP and CPP epitopes that are, respectively, the haptens in the corresponding antigens differ by only a single $CH_2$ group. Nevertheless, inhibition of anti-CEP-KLH antibody binding by CPP-HSA is remarkably weak, i.e., 0.1% cross-reactivity. Even though inhibition of anti-CPP-KLH antibody binding by CEP-HSA is somewhat greater, the anti-CPP-KLH antibodies also exhibit a high structural specificity, i.e., 1.3% cross-reactivity. Neither antibody shows significant cross-reactivity with CHP-HSA, a pyrrolated protein which contains a much larger carboxyalkyl group than the haptens against which either of the antibodies were raised. The pyrrolated protein, PP-6-ACA-BSA, which contains an n-pentyl rather than a carboxyalkyl sidechain, showed no cross-reactivity with either of the antibodies.

TABLE 2

Selectivity of rabbit polyclonal anti-CEP-KLH and anti-CPP-KLH antibody

| | anti-CEP-KLH antibody | | | | anti-CPP-KLH antibody | |
|---|---|---|---|---|---|---|
| | CEP-BSA Coating | | CEP-GPDH Coating | | (CPP-BSA Coating) | |
| | IC50 (pmol/well) | % Cross-reactivity | IC50 (pmol/well) | % Cross-reactivity | IC50 (pmol/well) | % Cross-reactivity |
| 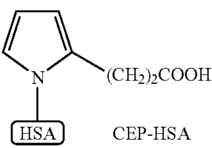 CEP-HSA | 0.02 | 100 | 0.38 | 100 | 12 | 1.3 |
| 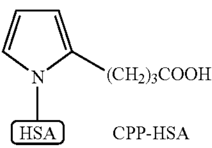 CPP-HSA | 19 | 0.1 | 1511 | 0.02 | 0.15 | 100 |
| 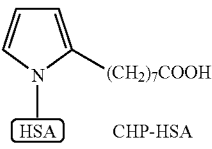 CHP-HSA | 24 | 0.1 | 802 | 0.05 | 62 | 0.24 |
| 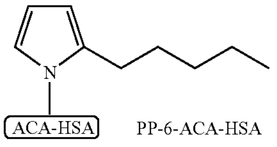 PP-6-ACA-HSA | N.D. | 0 | 4097 | 0.01 | N.D. | 0 |

Similar structural selectivity of anti-CEP-KLH antibody was observed when a different coating agent, CEP-GPDH, was used (FIG. 3B). The cross-reactivity of CPP-HSA and CHP-HSA was even lower with the CEP-GDPH coating agent than with the CEP-BSA coating agent, i.e., 0.02% and 0.05% respectively. As expected, GPDH itself was not recognized by anti-CEP-KLH antibody.

Example 2

Proposed Mechanism for Production of CEP-Protein Adduct in Vitro

To test the hypothesis that protein-bound CEPs can be generated by the reaction of HOHA-phospholipids with proteins, we prepared an ester (HOHA-PC) of HOHA with 2-lyso-phosphatidylcholine (PC).

Figure 6:
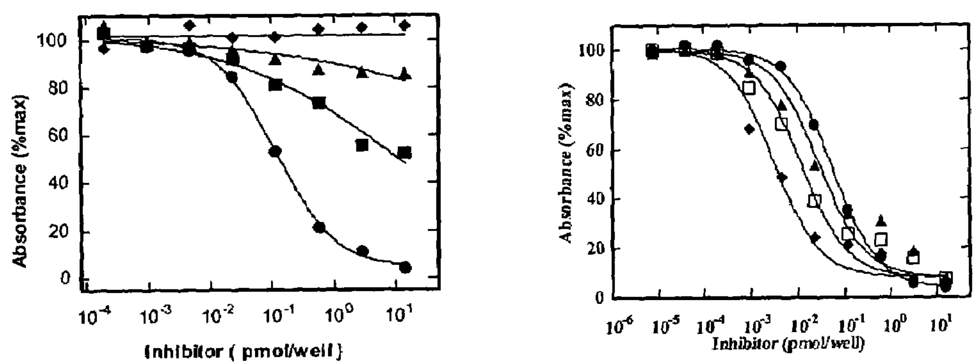
FIG. 6. Inhibition curve for binding of anti-CEP-KLH to CEP-BSA by CEP-HSA (●) and (A) products from reaction of HOHA-PC with HSA for 1 h (♦), 8 h (▲), 24 h (■) at 37°

Generation of CEP Immunoreactivity by the Reaction of HOHA-PC with HSA. Reaction of HOHA-PC with HSA results in generation of immunoreactivity toward anti-CEP-KLH antibodies. However, the inhibition curves do not parallel that for the CEP-HSA standard (FIG. 6A). This is presumably because the CEP epitopes generated are mostly in the form of PC esters rather than free acids against which the antibodies were raised. If the reaction product mixture is treated with KOH, ester hydrolysis converts CEP esters into the corresponding free acids whose inhibition curves parallel that for CEP-HSA (FIG. 6B). The yield of CEP epitope was 0.5% after 24 h based on phospholipid (Table 3).

TABLE 3

Generation of CEP epitope in the reaction of HOHA-PC with HSA.

| Time (h) | (pmol/ml) | Yield (%) |
|---|---|---|
| 1 | 740 | 0.04 |
| 2 | 1760 | 0.09 |
| 4 | 1900 | 0.1 |
| 8 | 5200 | 0.3 |
| 24 | 8820 | 0.5 |

Generation of CEP Immunoreactivity by Oxidation of DHA or DHA-PC in the Presence of HSA. Oxidation of DHA for 72 h in the presence of HSA resulted in the generation of a barely detectable level (0.4 pmol/mL) of CEP immunoreactivity that corresponds to only $7\times10^{-5}$% tield based on DHA (Table 4). Similar oxidation of AA for 72 h in the presence of HSA resulted in the generation of CPP immunoreactivity that corresponds to $40\times10^{-5}$% yield based on AA. Generation of cross-reacting epitopes was lower or undetectable. A somewhat higher yield (0.02%) of carboxyalkyl pyrrole immunoreactivity was generated upon oxidation of LA in the presence of HSA.

TABLE 4

In vitro oxidation (72 h) polyunsaturated fatty acids (PUFAs) in the presence of HSA.

| Antibody | PUFA | Immunoreactivity pmol/mL (yield) | Hapten |
|---|---|---|---|
| Anti-CEP-KLH | DHA | 0.4 ($7 \times 10^{-5}$%) | CEP |
| Anti-CPP-KLH | AA | 2.7 ($40 \times 10^{-5}$%) | CPP |
| Anti-CHP-KLH | LA | 142 (0.02%) | CHP |

Oxidation of DHA-PC for 24 h in the presence of HSA resulted in the generation of barely detectable CEP immunoreactivity (FIG. 7). Since the PC ester of CEP epitopes is not expected to be recognized by anti-CEP-KLH antibodies, the low level of immunoreactivity observed presumably results from hydrolysis of a small portion of the ester. As expected, much higher levels ($4\times10^{-4}$% yield after 24 h oxidation) of CEP immunoreactivity were generated if the product from oxidation of DHA-PC in the presence of HSA was treated with KOH to hydrolyze PC esters to the corresponding free acids. Thus, DHA-containing lipids are oxidatively cleaved to HOHA-containing lipids and which react with primary amino groups (e.g., in proteins to produce CEPs, mostly as CEP esters).

Example 3

CEP Epitopes in Retina. We used rodent retina as a test tissue to evaluate the pattern of immuno-labeling with anti-CEP-KLH antibodies that detect CEP epitopes. This tissue was chosen since the retina in a variety of species is known to be rich in DHA (Alvarez, R. A., et al., *Invest Ophthalmol Vis Sci* 35 402–8; Wang, N. and Anderson, R. E. (1992) *Curr Eye Res* 11:783–91.). DHA is not uniformly distributed throughout the retina but, rather, is concentrated in the light-sensitive photoreceptor rod outer segment (ROS) membranes and in the retinal pigment epithelium (RPE). DHA in these locations exists within an environment where photo-excitation occurs and oxygen levels and are most abundant, i.e., at the photoreceptor-RPE interface (Koutz, C. A., et al. (1995) Effect of dietary fat on the response of the rat retina to chronic and acute light stress. *Exp. Eye Res.* 60 307–16.).

Immunohistochemical staining of retina from mouse by the anti-CEP-KLH antibody is intense in the photoreceptor/retinal pigmented epithelial complex (FIG. 8). Lighter staining is also evident in the inner plexiform layer (IPL). In the photoreceptor layer, the outer segments (OS) are intensely stained while the photoreceptor inner segments (IS) are unlabeled. In contrast, when the anti-CEP-KLH antibody was preincubated with CEP-protein antigen, all labeling was eliminated.

Example 4

CEP Immunoreactivity in Plasma of Subjects with AMD.

Human plasma obtained from patients diagnosed with AMD and normal controls was prepared as described previously (Salomon, R. G., Batyreva, E., Kaur, K., Sprecher, D. L., Schreiber, M. J., Crabb, J. W., Penn, M. S., DiCorletoe, A. M., Hazen, S. L. and Podrez, E. A. (2000) Isolevuglandin-protein adducts in humans: products of free radical-induced lipid oxidation through the isoprostane pathway. *Biochim Biophys Acta* 1485 225–35). A metal chelator $Na_2$EDTA, and the antioxidant butylated hydroxytoluenl (BHT) were used to prevent artifacts generated by in vitro oxidation, and a cocktail of protease inhibitors was added to prevent protein degradation. All plasma samples were quench frozen immediately in liquid nitrogen.

The levels of CEP-protein adducts in human blood were measured by ELISA using polyclonal anti-CEP antibody. We examined the plasma of (i) 19 patients with diagnosed AMD of average age 82 years, designated AMD, (ii) 19 volunteers of average age 83 years who were diagnosed not to have AMD, designated N (83), (iii) 9 young healthy volunteers of average age 27 years, designated N (27) (FIG. 10). Comparison of levels of CEP-protein adducts in each group is presented in FIG. 10, and the mean levels of CEP-protein adducts (+/−S.D.) are summarized in Table 5. The results of statistical analyses are shown in Table 6.

The mean CEP adduct level is relatively higher in the plasma of AMD patients (15.9 pmol/ml) than in the plasma of younger or older volunteers (10.5 pmol/ml) who do not have documented AMD. Independent t-test analysis of the data showed that the difference of mean CEP immunoreactivity between AMD and both older (N83) and younger controls (N27) is significant (p=0.004 between AMD and N(83), p=0.05 between AMD and N(27)). No significant difference was found in the plasma of older versus younger controls (p=0.97).

TABLE 5

Levels (mean +/− S.D.) of CEP protein adducts in plasma

| | AMD | N (83) | N (27) |
|---|---|---|---|
| Population | 19 | 19 | 9 |
| Ages | 82 | 83 | 27 +/− 7 |
| CEP-protein (pmol/mL) | 15.9 +/− 7.4 | 10.5 +/− 2.8 | 10.5 +/− 3.7 |

TABLE 6

Two tailed P-values for independent student t-test between all 3 groups of individuals for CEP immunoreactivity.

| | AMD (19) | Aged NL (19) | Younger NL (9) |
|---|---|---|---|
| AMD (19) | — | 0.004 | 0.05 |
| Aged NL (19) | 0.004 | — | 0.97 |

A typical inhibition curve for binding of anti-CEP-KLH with an epitope in plasma of a patient with documented AMD, and a normal control is shown in FIG. 9. Noteworthy is the similarity of slope compared to the CEP-HSA standard, which supports the presumption that the epitope in human plasma is the same as that in the CEP-HSA. The binding inhibitions observed correspond to 32 pmol/mL (AMD), and 13 pmol/mL (Normal) of CEP immunoreactivity.

Example 6

Detection of Anti-CEP Adduct Antibodies in Plasma from Patients with AMD

A. Materials and Methods

A 96 well plate was coated with CEP-BSA (100 μL). As a blank, BSA (2%, 100 μL) was used. The plate was incubated for 1 h at 37° C., washed with PBS (10 mM, 300 μL) 3 times and blocked with CEO (1%, 300 μL) for 1 h at 37° C. Then, the plate was washed once with 0.1% chicken egg ovalbum (CEO) plus 0.05% Tween 20 (300 μL). The plate was loaded with plasma, diluted 20 times with 0.2% CEO plus 0.05% Tween 20, and incubated for 1 h at room temperature. The plate was washed 3 times with 0.1% CEO plus 0.05% Tween 20 (300 μL). Secondary antibodies were added (alkaline phosphatase conjugated goat anti-human IgG or alkaline phosphatase conjugated goat anti-human IgM, diluted 1:4000 with 1% CEO plus 0.05% Tween 20 (100 μL). The plate was washed 3 times with 0.1% CEO plus 0.05% Tween 20 (300 μL). A solution of disodium nitrophenyl phosphate (10 mg) in glycine buffer (11 mL, 50 mM, pH 9.6) with $MgCl_2$ (1 mM) was added. After 60 min, the absorbance was read at 405 nm with reference at 650 μm. The titre was defined as the ratio of plasma binding to antigen (A) vs. binding to BSA ($A_o$).

B. Results

ELISA was used to study, and quantify the generation of autoantibodies against CEP-derived protein adducts in human plasma. In these studies, CEP-BSA was used as antigen to coat the 96-well microplate, and BSA was used as non-specific control. The titre was defined as the ratio of the same plasma binding to CEP-modified BSA versus native BSA. Data obtained from triplicate or quadruplicate assays are summarized in Table 7. Plasma from 19 AMD patients showed an average titre of 3.4±3.1 for IgG autoantibodies binding the CEP-protein antigen, whereas, the average titre in 19 older volunteers, N(83), was 1.5±0.4 which is more than 50% lower compared with the AMD cohort (Table 7). Statistical analysis (student t-test) revealed that the difference between these two data sets is significant (P=0.02). High titre was assigned as any $A/A_o$ value greater than 2 S.D. above the average titre of N(83), which means $A/A_o>2.3$. Therefore, the prevalence of high anti-CEP autoantibody titres in AMD patients was 53% (10/19) compared with 21% (4/19) of the age-matched controls, N(83).

TABLE 7

Levels of anti-CEP autoantibodies in AMD and age-matched controls (N(82))

| | Population | Average $A/A_o$ ± SD | # of people with $A/A_o$ > or = 2.3 (Average N(83) + 2SD) | % of people with $A/A_o$ > 2.3 |
|---|---|---|---|---|
| AMD | 19 | 3.4 ± 3.1 | 10 | 53 |
| N(83) | 19 | 1.5 ± 0.4 | 4 | 21 |

*t-test: P = 0.02

Example 7

Level of CEP Adducts in Subjects with Atherosclerosis.

In 7-mL vacutubes (purple top) containing EDTA (10.5 mg), blood was collected from ten (10) patients diagnosed with atherosclerosis and from healthy volunteers (N(27), and N(82)). Cells were removed by centrifugation at 2500 rpm (1300 g) for 30 min. After transfer of the supernatant to plastic vials, butylated hydroxytoluene (BHT; 1 mg/mL), and protease inhibitors, leupeptin (35 μM), pepstatin (5 μM), and aprotinin (0.1 TIV/mL), were added. These vials were quench-frozen by placing in liquid nitrogen for 1 min and then stored at −80° C. until use.

ELISA of plasma from the 10 atherosclerosis patients and healthy volunteers was performed as described above in Example 4. A dilution factor of 0.2 was employed. The results are shown in FIG. 13 and Tables 8 and 9 below.

TABLE 8

Mean levels (±SD) of CEP immunoreactivity in plasma

| | Atherosclerosis | Normal (83) | Normal (27) |
|---|---|---|---|
| Average of age (year) | 58 | 83 | 27 |
| CEP (pmol/mL) | 40.1 ± 23.5 | 10.5 ± 2.8 | 10.5 ± 3.7 |

TABLE 9

Two tail of P-values for independent student t-test between all 3 groups of individuals for CEP immunoreactivity.

| | Atherosclerosis | Normal (83) | Normal (27) |
|---|---|---|---|
| AS | — | 4.6e−06 | 0.001 |
| N (82) | 4.6e−06 | — | 0.97 |

In view of the relatively low levels of DHA-containing lipids in the blood, it is surprising that the mean CEP adduct level is much higher in the plasma of atherosclerosis patients (40.1 pmol/ml) than in the plasma of aged or younger volunteers (10.5 pmol/ml) who do not have documented AS. Independent t-test analysis of the data showed that the average plasma CEP immunoreactivity is significantly different between patients (atherosclerosis) and non-patient controls (N83 and N27)). (p=4.6e−06 between atherosclerosis and N(83), p=0.001 between atherosclerosis and N(27). This high difference in CEP epitope levels found in the blood of patients with atherosclerosis compared to healthy volunteers indicates that CEP-based tests are useful for detecting atherosclerosis in patients suspected of having cardiovascular disease.

Example 8

Preparation, Characterization, and Applications of Monoclonal Anti-CEP-KLH Antibodies Monoclonal antibodies immunospecific for CEP adducts were produced in collaboration with the the Hydrodoma Core Facility at the Cleveland Clinic Foundation. A CEP-KLH antigen was used to obtain twenty-eight different single cell clones producing monoclonal anti-CEP-KLH antibodies that were identified and tested further by Western blot analysis against CEP-HSA as a standard protein containing the CEP modification. Five clones exhibiting the strongest apparent immunoreactivity were grown in larger amounts. Monoclonal anti-CEP-KLH antibody from these clones was purified essentially as described for the polyclonal anti-CEP-KLH antibody, except Protein A columns were used instead of Protein G columns. The protein concentrations of the purified monoclonal anti-bodies were determined by the Bradford method (M. M. Bradford, *Anal Biochem* 72, 248–54 (May 7, 1976) and Western analysis performed with control proteins using methods and chemiluminescence detection described elsewhere (J. W. Crabb, et al., *J Biol Chem* 266 16674–83 (Sep. 5, 1991), B. N. Kennedy, et al., *J Biol Chem* 273, 5591–8 (Mar. 6, 1998)). Comprehensive characterization of the specificities of two of these antibodies, designated anti-CEP monoclonal antibody 3 (in Ab3) and anti-CEP monoclonal antibody 4 (mAb4), was pursued.

A. Preparation and Characterization of Monoclonal Anti-CEP Antibodies

Immunization. Four Balb/c mice were used for monoclonal antibody production. Two mice received intraperitoneal (IP) injections of the immunogen (CEP-KLH) and the remaining two received subcutaneous (Sub-Q) injections of the same immunogen. All mice were ear tagged and identified by number.

Initial injection—the immunogen preparation was mixed with an equivalent volume of Complete Fruend's Adjuvant (Sigma, F-5881, CFA). For the IP injections, 0.25 ml the antigenic solution was emulsified with 0.25 ml CFA. The mouse received 0.5 ml of the emulsion utilizing a 25 g needle. The animals received their second injection two weeks after the first injection. The second injections were given utilizing the same route and volume as the initial injection. Incomplete Fruend's Adjuvant (Sigma, F-5506, IFA) was used for this and all subsequent injections. Three weeks latter a third injection was given.

Ten to fourteen days following the third injection a blood sample was collected from each mouse. The mice were anesthetized with Halothane in the CCF animal facility. When the mice showed no response to the foot pinch test, they were restrained by hand and the retro orbital sinus was punctured with the tip of a 250 μl non-heparinized capillary tube (Fisher cat# 02-668-10). Approximately 200 μl of blood was collected from each mouse. After the bleed the mice were returned to their respective cages to recover.

Serum was prepared and tested from each blood sample. The titer of the sera was determined whether the mouse received any additional immunizations or bleeds. If the titer was not satisfactory the mouse was reinjected as described above and bled after 10–14 days. Once a satisfactory titer was established from any 1 of the 4 mice, a fusion was initiated.

To prepare for the fusion, three weeks after the last IP injection, the mouse with the highest titer was injected intravenously (IV) with 0.1 ml of the sterile antigenic solution without adjuvant utilizing a 27 g needle. The mouse was restrained with a small rodent restraint for this injection.

Three days post IV injection the mouse was anesthetized and bled as previously described. After the bleeding, the mouse was euthanized via Halothane inhalation and the spleen acceptically removed.

Fusion protocol. All fusion work was done in a cell culture laminar flow hood and under sterile conditions. A suspension of myelomas cells (Sp2/0-Ag14 cells, ATCC cat# CRL-1581) to spleen cells at a ratio of 1:1 to 1:2 was prepared. The myeloma:spleen cell suspension was centrifuged and the supernatant carefully aspirated off of the mixed pellet. 1 ml of the 50% PEG solution added to the pellet over a one minute period. After the PEG was added, the tube was incubated in a 37° C. water bath for one minute. After the one minute incubation, 1.0 ml of DMEM+PS was added to the tube over one minute then 15 ml of DMEM+PS was added over a three minute period. After the media was added, the tube was centrifuged described above. The final pellet was resuspended in DMEM+PS+10% FBS+1×2-mercaptoethanol (Sigma, cat# M-7522, 100×=0.035%)+1× Hypoxanthine-Thymidine (Gibco, cat# 11067-030, 100× HT)+10% Hybridoma Cloning Factor (Origin, HCF) at a concentration of $8 \times 10^5$ original myeloma cells per ml of media. As a control, 2.0 ml of a suspension of unfused myeloma cells was prepared at $8 \times 10^5$ cells per ml in the same media. The fused cell suspension (100 μl) was added to the inner 60 wells in 96 well plates (Falcon 353072). The unfused myeloma cell suspension (100 μl) was added to a minimum of 12 wells. Approximately 300 ul of sterile milliQ water was added to the outer most wells. Plates were incubated for 24 hours at 37° C. with 10% $CO_2$ and humidity. After 24 hours, 100 ul of DMEM+PS+10% FBS+1× ME+1×HT+2× Aminopterin (Sigma, cat# A5159, 50×A)+10% HCF was added to all wells including the control wells with unfused myeloma cells. Every three days 50 ul of this media was added to the fusion wells.

Clonal Selection. At approximately 5 days post fusion the initial signs of viable hybridoma colonies were observable in the wells. In conjunction the wells containing unfused myeloma cells were dead or dying. By 12–14 days post fusion the hybridoma colonies were macroscopically visible and ready for assay by ELISA for antibody containing wells. ELISA evaluation of over 1500 wells was performed essentially as described for polyclonal antibody titer but using anti-mouse IgG as the secondary antibody. Positive wells producing anti-CEP antibody were selected by limiting dilution cloning in DMEM+PS+10% FBS+10% HCF. Approximately 4 days after cloning, each well was examined to identify colonies derived from a single cell.

B. Specificity of Monoclonal Antibodies.

To assess the structural specificity and selectivity of the monoclonal anti-CEP-KLH antibodies, mAb3 and mAb4, competitive inhibition of antibody binding to CEP-modified proteins by various haptens was examined. For all cross-reactivity studies, CEP-BSA was used as coating agent and CEP-HSA was used as a standard. The concentration at 50% inhibition ($IC_{50}$) for CEP-HSA was defined as 100% cross-reactivity. Duplicates of serial dilutions of all inhibitors were used and final curves were constructed using mean absorbance values. The mAb4 binds more strongly with the CEP-BSA. Its $IC_{50}$ (1.989 pmol/well) is about 4 times less than that of mAb3 ($IC_{50}$=7.661 pmol/well).

For various pyrrole modifications of the HSA, both mAb3 and mAb4 show remarkable selectivity (Table 10). When the carboxyalkyl side chain is extended from two to three $CH_2$ groups, i.e., from CEP-HSA to CPP-HSA, a cross-reactivity of only 0.3% is found with mAb4, and 0.2% with mAb3. Also, CHP-HSA which has an even longer side chain, i.e. with 7 $CH_2$ groups and a carboxylic acid at the end, exhibited a cross-reactivity of 0.3% with both antibodies. PP-HSA, that lacks the carboxyl group present in the CEP hapten against which these antibodies were raised, displayed little affinity for both antibodies. HSA itself was not recognized by these antibodies at all.

TABLE 10

Specificity of Monoclonal Antibodies.

| | | CEP-HSA | CHP-HSA | CPP-HSA | PP-HSA | HSA |
|---|---|---|---|---|---|---|
| mAb4 | $IC_{50}$ | 1.989 | 628 | 407 | 262111 | 4e+8 |
| | % Crossreactivity | 100 | 0.3 | 0.3 | 7e−4 | ND |
| mAb3 | $IC_{50}$ | 7.661 | 3028 | 2367 | 249061 | 4e+8 |
| | % Crossreactivity | 100 | 0.2 | 0.3 | 3e−3 | ND |

C. CEP Immunoreactivity in Mouse Retina

Mouse tissues were obtained from BALB/C mice after $CO_2$ asphyxiation and cervical dislocation. Eyes were gently opened with a cut through the eye wall with a razor blade posterior to the limbus, and were immersion fixed in a solution of 4% formaldehyde (freshly prepared from paraformaldehyde), in phosphate buffer (0.1 M, pH 7.2). After overnight fixation, tissues were rinsed in several changes of PBS and processed for paraffin microscopy using conventional procedures. Sections, cut at 3 μm, were placed on Superfrost slides. Sections were deparaffinized with xylene and hydrated through graded ethanols.

Tissue sections were incubated with 6% BSA in phosphate buffer (0.1 M, pH 7.2) for 30 min to block non-specific binding, then incubated for 16 h at 4° C. with anti-CEP antibody, i.e., anti-DOHA-KLH (diluted in 6% BSA/PBS 1:100). For control sections, anti-CEP antibody was pre-incubated with CEP-HSA or CPP-HSA. After washing extensively with PBS, sections were treated with goat-anti-rabbit IgG conjugated to peroxidase ABC (Vector Labs, Burlingame, Calif., 1:200 dilution) for 1 h at room temperature. Sections were washed with PBS and incubated in 0.05% DAB (3,3'-diaminobenzidine, Sigma Chemical Co., St. Louis, Mo.) and 0.03% hydrogen peroxide in the phosphate buffer at room temperature. Sections were viewed without counterstaining using DIC microscopy. The images presented were digitized with a Hamamatsu CCD camera, manipulated in Adobe Photoshop and assembled in Microsoft PowerPoint.

Immunoreactivity in Mouse Retina. Immunostaining of mouse retina using monoclonal antibody, mAb4, revealed the presence and localization of CEP adducts. As found previously with polycolnal rabbit anti-CEP-KLH antibody, CEP immunoreactivity was prominent in the RPE and photoreceptor outer segment (POS), where DHA is most abundant and oxygen levels are high. However, no CEP adducts were detected in other areas of retina, in contrast to immunostaining of rat retina by the rabbit polyclonal anti-CEP-KLH antibody, which exhibited less selective immunostaining.

What is claimed is:

1. A method of diagnosing an age-related macular degeneration (AMD) in a test subject, comprising:

determining levels of 2-(ω-carboxyethyl) pyrrole (CEP) adducts in a bodily fluid obtained from the test subject, wherein the presence of elevated levels of CEP adducts in the test subject's bodily fluid as compared to a predetermined value based on levels of CEP adducts found in a corresponding bodily fluid obtained from control subjects indicates that the test subject is more likely to have AMD than a test subject whose levels of CEP adducts in the bodily fluid are equal to or less than the predetermined value.

2. The method of claim 1 wherein the bodily fluid is whole blood, serum, or plasma.

3. The method of claim 1, wherein levels of CEP adducts in the bodily fluid are determined by contacting the bodily fluid with an anti-CEP antibody and assaying for the formation of an antigen-antibody complex between said antibody and CEP adducts in the bodily fluid.

4. The method of claim 1, wherein an antioxidant, protease inhibitor, or both have been added to the bodily fluid following isolation of the bodily fluid from the test subject.

5. The method of claim 1, wherein the predetermined value is obtained by determining levels of CEP adducts in a corresponding bodily fluid obtained from healthy subjects.

6. The method of claim 3, wherein the antibody is a monoclonal antibody.

7. The method of claim 3, wherein the antibody is a polyclonal antibody.

8. The method of claim 3, wherein the antibody has more than 100 fold greater affinity for a CEP adduct than a 2-(ω-carboxypropyl) pyrrole (CPP) adduct.

9. A method for diagnosising an age-related macular degeneration (AMD) in a test subject, comprising:

determining levels of CEP adducts in the blood, serum, or plasma of the test subject, wherein the presence of elevated levels of CEP adducts in the test subject's blood, serum, or plasma as compared to a value based on levels of CEP adducts found in the blood, serum, or plasma, respectively, of control subjects indicates that the test subject is more likely to have AMD than a test subject whose levels of CEP adducts in the blood, serum, or plasma are equal to or less than the value.

10. The method of claim 9, wherein an antioxidant, protease inhibitor, or both have been added to the bodily fluid following isolation of the bodily fluid from the test subject.

11. The method of claim 9, wherein levels of CEP adducts in the bodily fluid are determined by contacting the bodily fluid with an anti-GEP antibody and assaying for the formation of an antigen-antibody complex between said antibody and CEP adducts in the bodily fluid.

12. The method of claim 11, wherein the antibody is a monoclonal antibody.

13. The method of claim 11, wherein the antibody is a polyclonal antibody.

14. The method of claim 11, wherein the antibody has more than 100 fold greater affinity for a CEP adduct than a 2-(ω-carboxypropyl) pyrrole (CPP) adduct.

* * * * *

UNITED STATES PATENT AND TRADEMARK OFFICE

CERTIFICATE OF CORRECTION

PATENT NO. : 7,172,874 B2
APPLICATION NO. : 10/135196
DATED : February 6, 2007
INVENTOR(S) : Joe G. Hollyfield et al.

It is certified that error appears in the above-identified patent and that said Letters Patent is hereby corrected as shown below:

Claim 9, Column 22, line 19, please replace “diagnosising” with -- diagnosing --.

Claim 11, Column 22, line 36, please replace “anti-GEP” with -- anti-CEP --.

Signed and Sealed this

Twenty-fourth Day of April, 2007

JON W. DUDAS
*Director of the United States Patent and Trademark Office*